United States Patent [19]

Gerber

[11] Patent Number: 5,755,802
[45] Date of Patent: May 26, 1998

[54] KNEE-JOINT ENDOPROSTHESIS

[75] Inventor: Bruno E. Gerber, Maladière 45, 2007 Neuchâtel, Switzerland

[73] Assignee: Bruno E. Gerber, Neuchâtel, Switzerland

[21] Appl. No.: 513,954

[22] PCT Filed: Dec. 16, 1994

[86] PCT No.: PCT/EP94/04194

§ 371 Date: Aug. 30, 1995

§ 102(e) Date: Aug. 30, 1995

[87] PCT Pub. No.: WO95/17860

PCT Pub. Date: Jul. 6, 1995

[30] Foreign Application Priority Data

Dec. 30, 1993 [DE] Germany .......... 43 45 032.6

[51] Int. Cl.⁶ .................................................. A61F 2/38
[52] U.S. Cl. .................................................. 623/20
[58] Field of Search .................... 623/16, 18, 19, 623/20

[56] References Cited

U.S. PATENT DOCUMENTS

| | | |
|---|---|---|
| 4,016,606 | 4/1977 | Murray et al. . |
| 4,224,696 | 9/1980 | Murray et al. . |
| 4,936,853 | 6/1990 | Fabian et al. . |
| 4,950,297 | 8/1990 | Elloy et al. ................. 623/20 |
| 5,271,747 | 12/1993 | Wagner et al . |
| 5,395,401 | 3/1995 | Bahler ........................ 623/20 |

FOREIGN PATENT DOCUMENTS

| | | |
|---|---|---|
| 498586 | 8/1992 | European Pat. Off. . |
| 2663536 | 12/1991 | France . |
| 2705885 | 12/1994 | France . |
| WO9208424 | 5/1992 | WIPO . |

OTHER PUBLICATIONS

T.A.C.K. Knee-joint Prosthesis system, Waldemar Link GmbH & Co., Hamburg, Prospectus 3/92.

*Primary Examiner*—David J. Isabella
*Attorney, Agent, or Firm*—Knobbe, Martens, Olson & Bear, LLP

[57] ABSTRACT

Knee-joint endoprosthesis with a femoral part (10), a tibial part (11), and a bearing element (12) made of plastic, in particular polyethylene, disposed between the femoral and tibial parts, wherein the bearing element (12) is slidably supported on a spherically concave bearing surface (20) of the tibial part (11), which faces the femoral part (10). Above the tibial bearing surface (20) projects a peglike or rodlike stopping device (21), which enters an elongated opening (22) in the supporting and sliding surface (32) of the bearing element (12) that faces the tibial bearing surface (20), in such a way that the bearing element (12) can rotate on the tibial bearing surface (20) and also, to a limited degree, be displaced longitudinally in the plane of knee flexion.

19 Claims, 3 Drawing Sheets

KNEE-JOINT ENDOPROSTHESIS

FIELD OF THE INVENTION

The invention relates to a knee-joint endoprosthesis with a femoral part, a tibial part and a bearing element made of plastic, in particular polyethylene, which is disposed between the femoral and tibial parts in such a way that the bearing element is slidably seated on a bearing surface of the tibial part that faces the femoral part and is spherically concave in shape.

BACKGROUND OF THE INVENTION

A knee-joint endoprosthesis of this kind has been disclosed in U.S. Pat No. 4,224,696. This knee-joint endoprosthesis permits both a rotational movement and a sliding movement of the bearing element on the tibial bearing surface, with the consequence that the knee joint can continue to move in a nearly natural manner. The known knee-joint endoprosthesis does not, however, comprise structural features to ensure precise rotational and longitudinal guidance of the bearing element. Furthermore, there is a risk that the bearing element will "rock out" beyond the tibial bearing surface or tibial plate, toward either the front or the back.

Other knee-joint endoprostheses are known that enable only rotation of the bearing element relative to the tibial bearing surface, and do not allow transverse displacement (T.A.C.K. knee-joint prosthesis system of the firm Waldemar Link GmbH & Co., Hamburg, Prospectus 736 d-en 3.92). This knee-joint prosthesis does achieve a relatively uncomplicated structure, but because the bearing element can merely rotate, the natural movement of the knee joint is imitated to only a limited extent. On the other hand, means are provided to keep the bearing element seated on the tibial bearing surface. However, if the rotational movement should be excessive, here too there is a danger that the femoral part will be lifted away from the bearing element with the possible consequence of undesired luxation.

SUMMARY OF THE INVENTION

It is the object of the present invention to develop a knee-joint endoprosthesis of the kind described at the outset in such a way as to guarantee precise rotational and longitudinal guidance. Moreover, the bearing element is to be reliably prevented from "rocking out" beyond the tibial plate.

At the same time, however, the prosthesis is designed to ensure that, as in the natural knee, the resistance to flexion does not increase as the knee is flexed or bent by greater amounts.

This object is achieved in accordance with the invention by a knee-joint endoprosthesis including a femoral part, a tibial part, and a bearing element made of plastic, in particular polyethylene, which is disposed between the femoral and tibial parts. The bearing element is slidably supported on a spherically concave bearing surface of the tibial part which faces the femoral part. Advantageously, a stopping device projects above the tibial bearing surface and enters an elongated opening in the supporting and sliding surface of the bearing element that faces the tibial bearing surface. The stopping device and opening cooperate in such a way that the bearing element can rotate on the tibial bearing surface and also, to a limited degree, be displaced longitudinally in the plane of knee flexion. Also, the geometrical median long axis of the bearing surface of the tibial part is tilted backward from the median long axis of the extended knee-joint endoprosthesis, so that the tibial bearing surface in the implanted state is correspondingly inclined downward toward the back. In a particularly worthwhile feature, the stopping device is peglike or rodlike and comprises a cap screw with a head that can be screwed into the tibial bearing surface to hold the bearing element onto the tibial bearing surface. Another advantageous detail is the prevention of the bearing element from "rocking out" beyond the tibial bearing surface, while simultaneously the inclination of the tibial bearing surface in accordance with the invention keeps the resistance to flexion relatively small even in the end phase of knee bending or flexion, particularly in combination with a femoral part having a radius that becomes progressively smaller toward the back of the knee.

BRIEF DESCRIPTION OF THE DRAWINGS

In the following an embodiment of a knee-joint endoprosthesis in accordance with the invention is described in detail with reference to the attached drawings, wherein.

DESCRIPTION OF THE PREFERRED EMBODIMENTS

Figure 1:
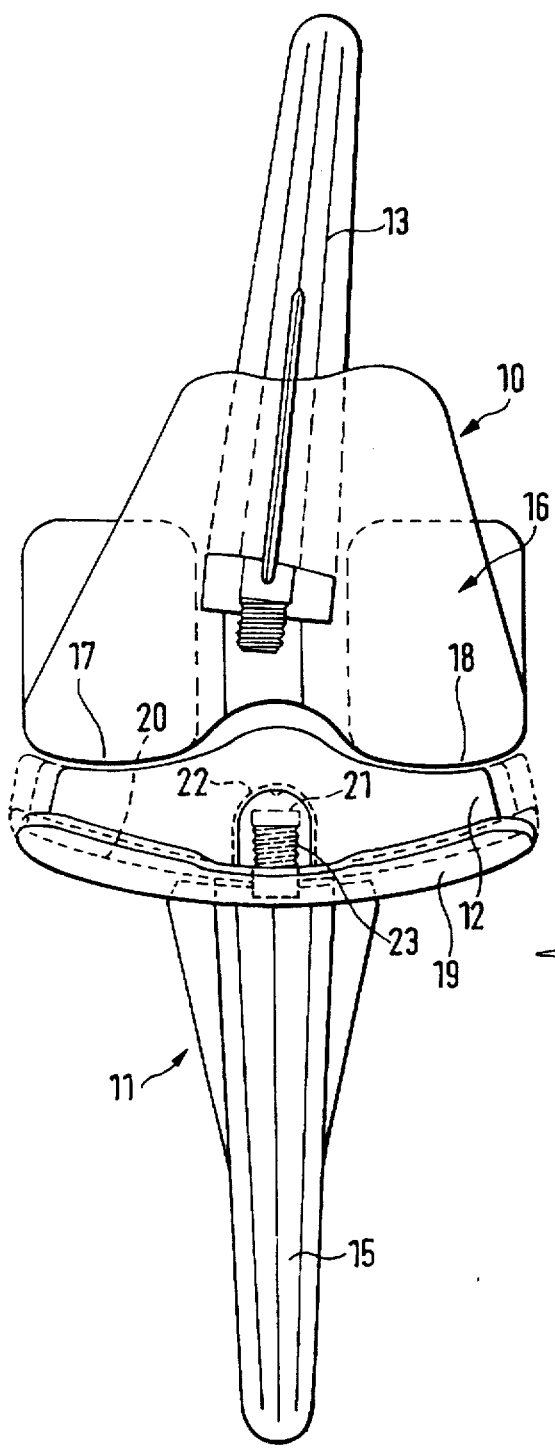
FIG. 1 is a front view of a knee-joint endoprosthesis in accordance with the invention in the implanted state.
Figure 2:
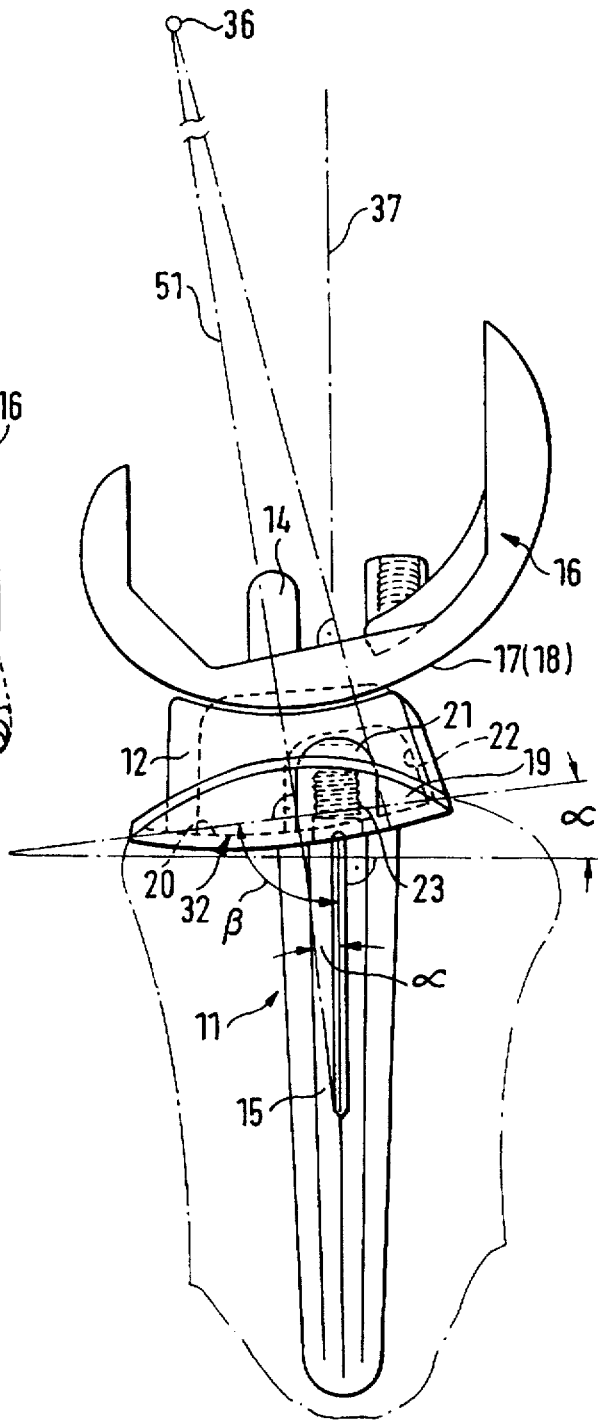
FIG. 2 is a side view of the knee-joint endoprosthesis shown in FIG. 1.

The knee-joint endoprosthesis shown in FIGS. 1 and 2 consists of a femoral part 10, a tibial part 11, and a bearing element 12 made of plastic, in particular polyethylene, which is disposed between the femoral and tibial parts. Femoral part 10 and tibial part 11 are fixed within their respective bones in a manner know per se, to the femur by spikes 13, 14 and to the tibia by spike 15. The femoral part further comprises a so-called femoral sled 16 with two convexly curved sliding surfaces 17, 18, which in the implanted state correspond to sliding surfaces with complementary concave curvature on the upper surface of the bearing element 12, so that a so-called rolling-sliding movement occurs between the bearing element 12 and the femoral sled 16.

To the end of the tibial part 11 toward the femoral part 10 a tibial bearing plate 19 is attached. The tibial bearing surface 20, which faces the femoral part 10, is curved spherically inward. The underside of the bearing element 12, facing the bearing surface, is correspondingly convex, so that the bearing element 12 is supported both rotatably and in such a way that it can slide in the plane of knee flexion, with no danger of being lifted away from the tibial bearing surface. To prevent the bearing element 12 from being displaced sideways out of the plane of knee flexion, the bearing element 12 is guided as it moves over the tibial bearing surface 20. For this purpose a peglike stopping device 21 projects upward from the tibial bearing surface 20 into an elongated opening 22 in the supporting or sliding surface of the bearing element 12, i.e. the surface that faces the tibial bearing surface 20, as can be seen in FIGS. 1 and 2. The peglike stopping device 21 is screwed onto the tibial bearing surface 20 (see screw thread 23 in FIGS. 1 and 2). Furthermore, the upper end of the peg 21, which points toward the femoral part 10, has a hemispherical shape. The cross section and the inner corners of the elongated opening or recess 22 in the bearing element 12 are matched in shape to the contour of the stopping peg 21. As a result, lateral play between bearing element 12 and tibial part 11 is avoided, i.e. the bearing element 12 is guided precisely over the tibial part 11 in the plan of knee flexion. Because of the shape of the stopping peg 21 as described here, the tibia is not prevented from rotating relative to the femur.

Figure 6:
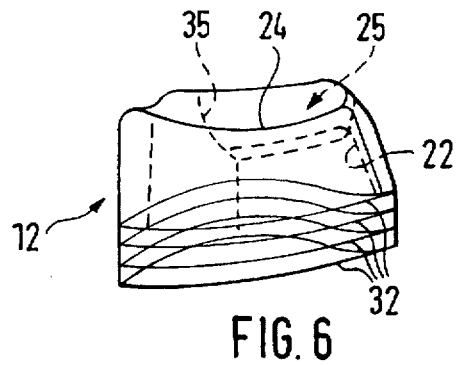
FIG. 6 is a side view of the bearing element according to FIGS. 4 and 5, again showing various heights.
Figure 4:
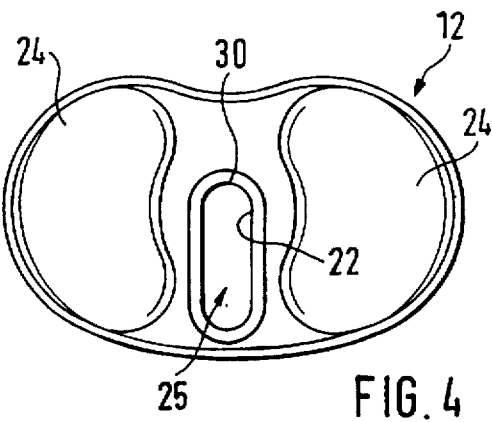
FIG. 4 shows in plan view a bearing element of plastic, in particular polyethylene, to be inserted between the femoral part and the tibial part.
Figure 5:
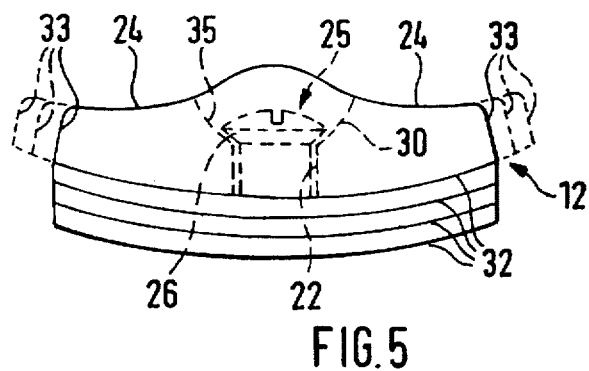
FIG. 5 is a front view of the bearing element according to FIG. 4, showing various heights and widths.
Figure 3:
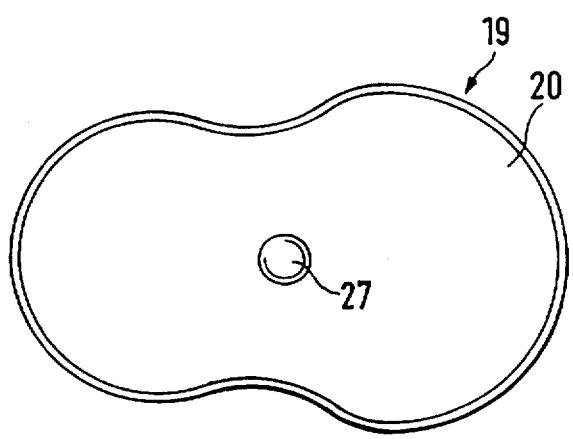
FIG. 3 shows the tibial bearing surface in plan view.
Figure 7:
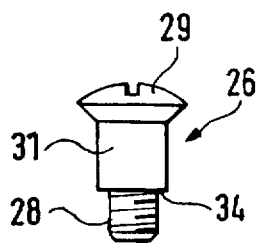
FIG. 7 shows a retaining screw for the bearing element according to FIGS. 4 to 6, to be attached to a tibial bearing surface according to FIG. 3.

It can be seen in FIG. 3 that the tibial bearing plate 19 is asymmetrical in plan view. The bearing element 12, shown in plan view in FIG. 4, is approximately kidney-shaped in outline. It is constructed in one piece and made of plastic, in particular polyethylene. The bearing shells associated with the convex sliding surfaces 17, 18 of the femoral sled 16 are identified in FIG. 4 by the reference numeral 24. The elongated opening 22 in the bearing element 12, mentioned above with reference to FIGS. 1 and 2, in the embodiment according to FIGS. 4 to 6 is constructed as a slotlike aperture 25 that forms a passage through the bearing element. Through this aperture can be inserted the threaded part and shaft of a cap screw 26 such as is shown, for example, in FIG. 7. The cap screw 26 is screwed into the tibial bearing plate 19 by way of the latter's bearing surface 20. The corresponding threaded bore is identified in FIG. 3 by the reference numeral 27. The complementary threaded section of the cap screw 26 is indicated by the reference numeral 28 in FIG. 7. The head 29 of the cap screw has a lens shape, as shown in FIG. 7. In the assembled state, as shown in FIG. 5, this screw head is recessed below the level of the bearing shells 24 of the bearing element 12, so that it cannot collide with the femoral sled 16. The lower surface of the screw head 29 is apposed to an inner rim 30 of the aperture 25, so that the cap screw 26 holds the bearing element 12 firmly against the bearing surface 20 of the tibial bearing plate 19, with no play. Between the screw head 29 and the threaded section 28 of the cap screw 26 according to FIG. 7 there is a cylindrical section 31, which is apposed with no clearance to the side walls of the slotlike aperture 25, so as to ensure precise guidance of the bearing element 12 in the plane of knee flexion.

The screw 26 can be provided with an internal thread instead of the threaded section 28, so that the screw 26 can be screwed onto a threaded peg at the upper end of the tibial spike 15.

The lines 32 in FIG. 5 and FIG. 6 indicate that the bearing element 12 can be made in different heights, whereas the lines 33 show the possible widths of the bearing element 12. That is, the drawings represent the variability of the bearing element 12 in both height and width.

The boundary surface 34 at the lower edge of the cylindrical section 31 of the cap screw 26 is planar. To fit it against the concave tibial bearing surface 20, a ring with convex curvature on one side is interposed.

All the parts with the exception of the bearing element 12 are preferably made of titanium or a titanium alloy. The bearing surfaces can additionally be covered with a ceramic layer.

With reference to FIG. 2 it should also be mentioned that an aspect of crucial significance to the knee-joint endoprosthesis described here is the tilted position of the spherically concave bearing surface 20, which slants down toward the back of the knee. The angle of the inclination with respect to the horizontal is identified by a. The angle $\beta$ between the spherically concave bearing surface 20 and the tibial axis, which coincides with the geometric median long axis 37 of the tibial spike 15, is smaller than 90° by the angle $\alpha$. The angle of inclination $\alpha$ is preferably 5° to 15°, in particular about 10°. Accordingly, the angle $\beta$ is 70° to 85°, in particular about 80°. The inclination of the spherically concave bearing surface 20 is defined by the slope of the line connecting the two end points of the bearing surface in the plane of knee flexion (the plane of the drawing in FIG. 2). It follows that the geometrical center of curvature 36 of the spherically concave bearing surface 20 of the tibial part 11 is also displaced backward from the median long axis 37 of the tibial spike 15, which coincides with the tibial axis and hence with the median long axis of the extended knee-joint endoprosthesis, i.e. the knee-joint endoprosthesis in its configuration when the leg is extended. Because of the backward tilt of the spherically concave bearing surface 20 of the tibial part 11, which has just been described, the resistance to flexion does not increase in the end phase of knee flexion, as is also the case in the natural knee. Furthermore, the spherical curvature of the bearing surface 20 also ensures that when the knee is fully flexed there is still sufficient resistance to prevent the bearing element from sliding beyond the back edge of the bearing surface.

In addition, the tibial spike 15 is displaced forward from the median long axis of the spherically concave bearing surface 20 of the tibial part 11 (again see FIG. 2). This position of the spike 15 relative to the spherically concave bearing surface 20 also increases the similarity to the natural knee joint at the proximal end of the tibia. In particular, force is thereby transmitted into the tibia in a direction perpendicular to the contact surfaces of the implant, so that even after a long period of use the tibial part is unlikely to work loose. The force transmission into the tibia is optimal.

The measures cited above and the resulting advantages are likewise not obvious from the state of the art according to the patent U.S. Pat. No. 4,224,696 mentioned at the outset.

Figure 8:
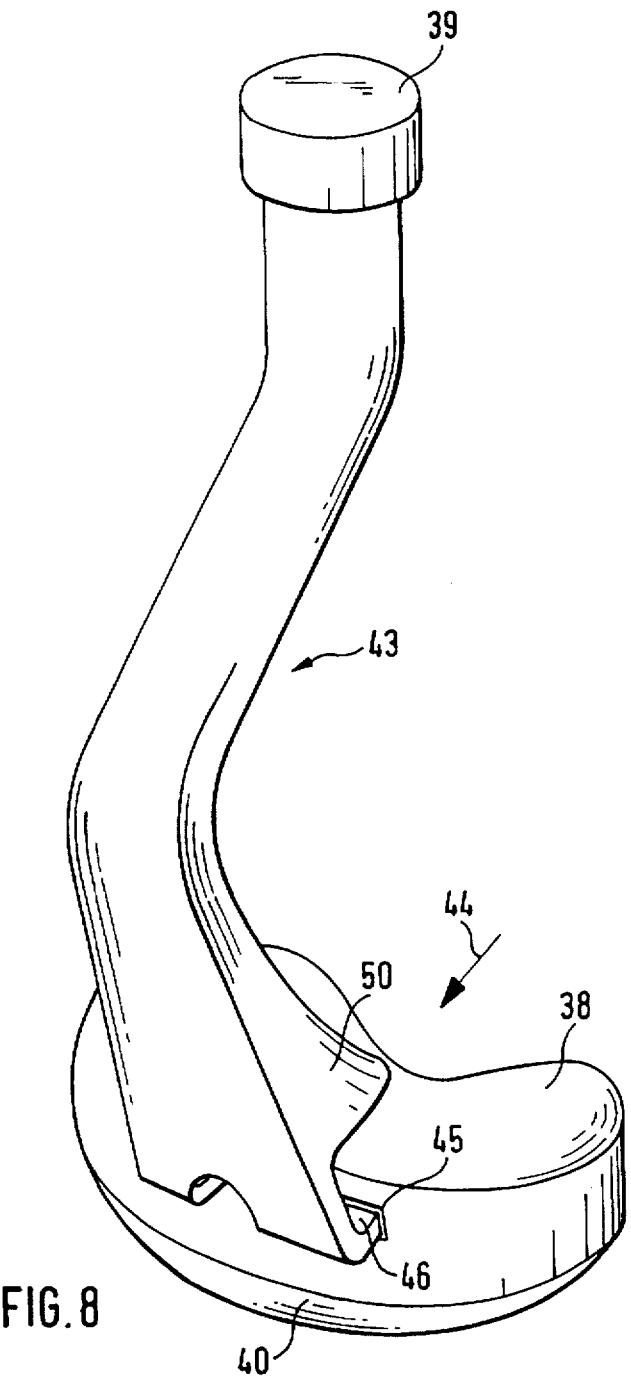
FIG. 8 shows an instrument with which to prepare the tibia for implantation of the tibial part of the knee-joint endoprosthesis in accordance with the invention, in perspective view.

As has been mentioned above, the tibial bearing surface 20 is formed by a spherically curved plate. This plate is about 1.0 to 2.0 mm thick, as a result of which only a minimal amount of bone material must be removed at the proximal end of the tibia. However, it is necessary to make the proximal end of the tibia correspondingly concave. For this purpose an instrument as shown in FIG. 8 is proposed; it is characterized by an impact device 43 with a distal tibia-shaping part 38 and a proximal striking surface 39, the former having a convex shaping surface 40 to produce a correspondingly concave curvature of the proximal end of the tibia. The tibia-shaping part 38 can be attached to the proximal end of the impact device 43 by pushing it in the direction of the arrow 44. The striking surface 39 is precisely aligned above the shaping surface 40, so that by hitting the striking surface 39 one or more times with a hammer or similar tool, the spongiosa at the proximal, initially planar cut surface of the tibia can be given an appropriately concave shape into which the tibial bearing plate 19 fits exactly, as indicated in FIG. 2.

Figure 10:
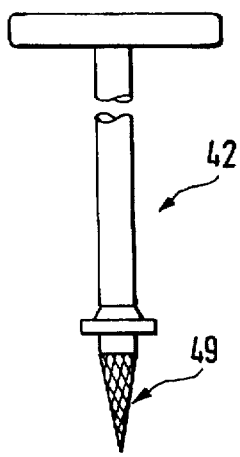
FIG. 10 is a side view of a rotary bone cutter for the tibia.
Figure 9:
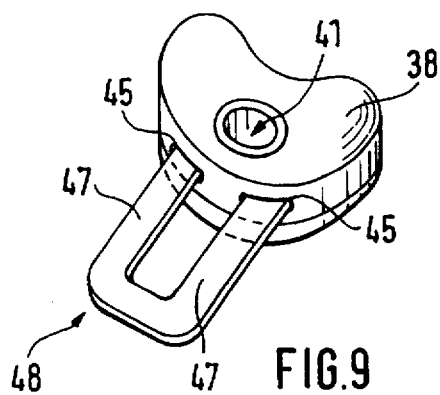
FIG. 9 shows part of the instrument according to FIG. 8 in perspective view.

After the shaping of the proximal cut surface of the tibia by means of the die-like shaping part 38 has been completed, a rotary bone cutter is inserted through the latter and used to prepare a bore for the tibial spike 15. As shown in FIG. 9, a bore 41 is provided in the tibia-shaping part 38 through which the above-mentioned bone cutter, shown in FIG. 10, can be passed. The bore 41 is so placed that the tibial spike-receiving bore can be positioned precisely with respect to the bearing surface 20 of the tibial part 11 that is to be implanted. So that the tibia-shaping part 38 can be fixed to the impact device 43, the tibia-shaping part 38 is provided with two transverse slits 45, only one of which is visible in FIG. 8. Into these transverse slits 45 a complementary holding fork 46 at the end of the impact device 43 can be introduced. The limbs 47 of a correspondingly formed U-shaped holder 48 can also be pushed into the transverse slits 45. The holder 48 can be used to hold the tibia-shaping part 38 in position while the tibial spike-receiving bore is being constructed by the bone cutter 42, which has been passed through the bore 41. The cutting section of the bone cutter 42, as can be seen in FIG. 10, is conical in shape and is identified by the reference numeral 49.

To transmit the force of the hammer strokes from the striking surface 39 of the impact device 43 to the tibia-shaping part 38, the distal end of the impact device 43 is provided with a projecting nose 50. This nose 50 is apposed to the upper surface of the tibia-shaping part 38 when the latter is attached to the impact device. Hence the impact force is transferred from the striking surface 39 through the shaft of the impact device 43 and the above-mentioned nose 50 onto the tibia-shaping part 38.

In FIG. 2 the words "back" and "front" identify the back and front of the knee joint. With reference thereto, it can be seen that the radius of the "back" part of the convex sliding surfaces 17, 18 of the femoral sled 16 is smaller than the radius of the "front" part of these sliding surfaces. This is one reason why it is kinematically advantageous for the spherically concave bearing surface 20 of the tibial part to slant down toward the back, as shown in FIG. 2.

All the characteristics disclosed in the application documents are claimed as essential to the invention, to the extent that they are new to the state of the art singly or in combination.

I claim:

1. A knee-joint endoprosthesis, comprising:
   a femoral part,
   a tibial part having a spherically concave bearing surface facing the femoral part,
   a bearing element disposed between the femoral and tibial parts and having a supporting and sliding surface facing the tibial bearing surface, wherein the bearing element is slidably supported on said tibial bearing surface;
   a shaft on the tibial part facing away from the tibial bearing surface having a geometrical median long axis forming an acute angle of between 5° and 15° with the geometrical median long axis of the tibial bearing surface in the implanted state; and
   a stopping device in the form of a cap screw fastened to the tibial bearing surface and having a head, wherein said cap screw projects above the tibial bearing surface and enters a slot-like aperture in the supporting and sliding surface of the bearing element to extend completely therethrough, the cap screw passing through the aperture so that its head engages an upper rim of the slot-like aperture recessed below the upper surface of the bearing element to retain the bearing element on the tibial bearing surface in such a way that the bearing element can rotate on the tibial bearing surface and also, to a limited degree, be displaced longitudinally in the plane of knee flexion, and that the geometrical median long axis of the spherically concave bearing surface of the tibial part is tilted backward from the median long axis of the extended knee joint endoprosthesis, so that the spherically concave bearing surface is correspondingly inclined downward toward the back.

2. A knee-joint endoprosthesis according to claim 1, wherein the contact surface of the screw head has a curvature in the long direction of the slotlike aperture that matches the concavity of the tibial bearing surface.

3. A knee-joint endoprosthesis according to claim 1, wherein the screw head is placed within, a transverse slot in the bearing element that extends parallel to the elongated opening.

4. A knee-joint endoprosthesis according to claim 3, wherein the screw-head contact surface of the transverse slot closer to the tibial bearing surface has a concave curvature in the long direction of the slot similar to the curvature of the tibial bearing surface.

5. A knee-joint endoprosthesis according to claim 1, wherein the stopping device comprises a titanium or a titanium alloy.

6. A knee-joint endoprosthesis according to claim 1, wherein the screw head is lens-shaped.

7. A knee-joint endoprosthesis according to claim 1, wherein the tibial spike is displaced forward relative to the median long axis of the spherically concave bearing surface of the tibial part.

8. A knee-joint endoprosthesis according to claim 1, wherein the tibial bearing surface is asymmetrical in plan view.

9. A knee-joint endoprosthesis according to claim 1, wherein the tibial bearing surface is formed by a plate shaped like a section of a sphere, the thickness of which is about 1.0 to 2.0 mm.

10. A knee-joint endoprosthesis according to claim 1, wherein the tibial spike is displaced forward relative to the median long axis of the spherically concave bearing surface of the tibial part.

11. A knee-joint endoprosthesis according to claim 1, wherein said cap screw includes a threaded aperture for engaging a threaded peg projecting from the tibial bearing surface.

12. A knee-joint endoprosthesis according to claim 1, wherein said acute angle is about 10°.

13. A knee-joint endoprosthesis, comprising:
    an upper femoral part;
    a lower tibial part including an upwardly facing spherically concave bearing surface;
    a bearing element made of plastic disposed between the femoral and tibial parts defining an elongated opening from a lower supporting and sliding surface facing the tibial bearing surface to an upper bearing surface cooperating with a bearing surface formed on the femoral part, the elongated opening including an upper recessed rim;
    a shaft on the tibial part extending in an opposite direction from the tibial bearing surface and having a geometrical median long axis forming an acute angle of between 5° and 15° with the geometrical median long axis of the tibial bearing surface in the implanted state; and
    a stopping device including an upper head for engaging the rim of the elongated opening and holding the bearing element onto the tibial bearing surface. the stopping device cooperating with the elongated opening so that the bearing element can rotate on the tibial bearing surface and be displaced longitudinally in the plane of knee flexion. wherein the geometrical median long axis of the tibial bearing surface is tilted backward from the median long axis of the extended knee-joint endoprosthesis so that the tibial bearing surface in the implanted state is inclined rearwardly downward.

14. A knee-joint endoprosthesis according to claim 13. wherein s aid acute angle is about 10°.

15. A knee-joint endoprosthesis according to claim 13. wherein the geometrical median long axis of the tibial shaft intersects the tibial bearing surface at a location forward from the center of the bearing surface.

16. A knees joint endoprosthesis according to claim 13. wherein the tibial bearing surface is asymmetrical in plan view.

17. A knee-joint endoprosthesis according to claim 13. wherein the tibial bearing surface is formed by a plate shaped like a section of a sphere. the thickness of which is about 1.0 to 2.0 mm.

18. A knee-joint endoprosthesis according to claim 13. wherein the stopping device for the bearing element is formed by a cap screw that can be threadingly fastened to the tibial bearing surface and the head of the cap screw engages the recessed rim.

19. A knee-joint endoprosthesis according to claim 18. wherein an underside of the cap screw head which contacts the recessed rim has a curvature in the long direction of the opening that matches the concavity of the tibial bearing surface.

* * * * *

UNITED STATES PATENT AND TRADEMARK OFFICE
CERTIFICATE OF CORRECTION

PATENT NO. : 5,755,802
DATED : May 26, 1998
INVENTOR(S) : Bruno E. GERBER

It is certified that error appears in the above-identified patent and that said Letters Patent is hereby corrected as shown below:

In Column 7, Line 11, change "s aid acute" to read --said acute--; and

In Column 7, Line 16, change "knees joint" to read --knee-joint--.

Signed and Sealed this

Twenty-seventh Day of October, 1998

Attest:

BRUCE LEHMAN

Attesting Officer  Commissioner of Patents and Trademarks